US008658981B2

(12) United States Patent
Lacey et al.

(10) Patent No.: US 8,658,981 B2
(45) Date of Patent: Feb. 25, 2014

(54) METHODS AND SYSTEMS FOR IMAGE DETECTION

(75) Inventors: Joseph James Lacey, Waukesha, WI (US); Russell Hum, Waukesha, WI (US); Ashutosh Joshi, Waukesha, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 13/209,150

(22) Filed: Aug. 12, 2011

(65) Prior Publication Data
US 2013/0039533 A1 Feb. 14, 2013

(51) Int. Cl.
*G01T 1/24* (2006.01)
(52) U.S. Cl.
USPC ................................. 250/370.15

(58) Field of Classification Search
USPC ............... 250/370.01–370.15, 362, 250/363.01–363.1; 378/98.8
See application file for complete search history.

(56) References Cited

U.S. PATENT DOCUMENTS

| 5,260,704 A * | 11/1993 | Hustig et al. ........... 341/144 |
| 2005/0190804 A1 * | 9/2005 | Robinson et al. ...... 372/29.015 |
| 2008/0103391 A1 * | 5/2008 | Dos Santos Varela ..... 600/436 |

FOREIGN PATENT DOCUMENTS

GB 2034992 A * 6/1980 ............. H03K 13/02

* cited by examiner

*Primary Examiner* — Kiho Kim (57) ABSTRACT

A method is provided for image detection. The method includes measuring a temperature of an analog-to-digital (A/D) converter of an imaging system during an imaging scan of an object, and correcting a gain of the A/D converter based on the measured temperature of the A/D converter.

13 Claims, 6 Drawing Sheets

METHODS AND SYSTEMS FOR IMAGE DETECTION

BACKGROUND OF THE INVENTION

The subject matter disclosed herein relates generally to methods and system for image detection.

Imaging systems are widely used to capture images of objects. For example, diagnostic images of a person or an animal may be obtained to assist a doctor or other health care professional in making an accurate diagnosis. Another example includes imaging luggage, shipping containers, and/or the like for security and/or industrial inspection applications. Imaging systems often include an energy source and detectors. Energy, for example x-rays, produced by the source travel through the object being imaged and are detected by the detectors. In response thereto, the detectors produce analog electrical signals that represents the sensed energy. Analog-to-digital (A/D) converters typically sample the analog data received from the detector(s) and convert the data to digital signals for subsequent processing and image reconstruction. The A/D converters may be components of the detectors or may be components of a controller that performs the subsequent processing and/or image reconstruction.

To conserve electrical power when an imaging system is not in use, portions of the electronics such as the A/D converters within an imaging system may be powered down when the imaging system is not in use. For example, digital sections (e.g., a digital clock) of the A/D converters may not be supplied with electrical power when the imaging system is idle. The portions of the A/D converters that have been powered down must be powered back up to perform an imaging scan of an object. The A/D converters experience an increase in temperature when the A/D converters are powered up. In some situations, the A/D converters do not reach their normal operating temperature range until after at least a portion of the imaging scan has been performed. However, the temperature of the A/D converters affects the gain of the A/D converters, and/or associated electronics such as a photodiode. Accordingly, the A/D converters may have different gains at different times during the imaging scan, which may cause errors within the resulting image and/or may result in lower image quality.

BRIEF DESCRIPTION OF THE INVENTION

In one embodiment, a method is provided for image detection. The method includes measuring a temperature of an analog-to-digital (A/D) converter of an imaging system during an imaging scan of an object, and correcting a gain of the A/D converter based on the measured temperature of the A/D converter.

In another embodiment, an imaging system includes a detector that is configured to generate analog electrical signals in response to received electromagnetic energy. The imaging system also includes an analog-to-digital (A/D) converter operatively connected to the detector for receiving the analog electrical signals generated by the detector. The A/D converter is configured to convert the analog electrical signals into digital electrical signals. A heat sink is engaged with a surface of the A/D converter for absorbing heat from the A/D converter.

In another embodiment, a method is provided for image detection. The method includes initiating at least one pre-scan activity of an imaging scan of an object, powering up at least a portion of an analog-to-digital (A/D) converter upon initiation of the at least one pre-scan activity, measuring a temperature of the A/D converter after the A/D converter has been powered up, and beginning the imaging scan once the measured temperature of the A/D converter is equal to or greater than a predetermined threshold temperature.

DETAILED DESCRIPTION OF THE INVENTION

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the term "reconstructing" or "rendering" an image or data set is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image. In an exemplary embodiment, the "object" being imaged is a human individual. However, the object may alternatively be of another living creature besides a human individual. Moreover, the object is not limited to living creatures, but rather may be of inanimate objects, such as, but not limited to, luggage, shipping containers, and/or the like.

Various embodiments provide imaging detectors, imaging controller/processors, imaging systems, and methods for imaging. For example, various embodiments of imaging detectors, imaging controller/processors, imaging systems, and methods for imaging measure a temperature of an analog-to-digital (A/D) converter of an imaging system during an imaging scan of an object, and correct a gain of the A/D converter based on the measured temperature of the A/D converter. Moreover, and for example, various embodiments of imaging detectors, imaging controller/processors, imaging systems, and methods for imaging include a heat sink engaged with a surface of the A/D converter for absorbing heat from the A/D converter. Furthermore, and for example, various embodiments of imaging detectors, imaging controller/processors, imaging systems, and methods for imaging initiate at least one pre-scan activity of an imaging scan of an object, power up at least a portion of an A/D converter upon initiation of the at least one pre-scan activity, measure a temperature of the A/D converter after the A/D converter has been powered up, and begin an imaging scan once the measured temperature of the A/D converter is equal to or greater than a predetermined threshold temperature. At least one technical effect of various embodiments is improved image quality and/or a reduced or eliminated amount of errors and/or artifacts within an image. At least one other technical effect of various embodiments is reducing the power consumption of an imaging system, reducing the size of a power supply of an imaging system, reducing a noise of an imaging system, and/or enabling power savings without compromising system readiness to scan.

The various embodiments may be implemented within imaging systems, which include computed tomography (CT) systems, magnetic resonance (MR) systems, ultrasound systems, positron emission tomography (PET) systems, nuclear medicine systems, and other types of imaging systems. Applications of image systems include medical applications, security applications, industrial inspection applications, and/or the like. An exemplary embodiment is described and illustrated herein with respect to a CT imaging system having detectors that detect x-rays. However, the various embodiments described and/or illustrated herein may be used with any other imaging modality and may be used to detect any other type of electromagnetic energy. Moreover, the various embodiments described and/or illustrated herein are applicable with single slice and/or multi-slice configured systems.

Figure 1:
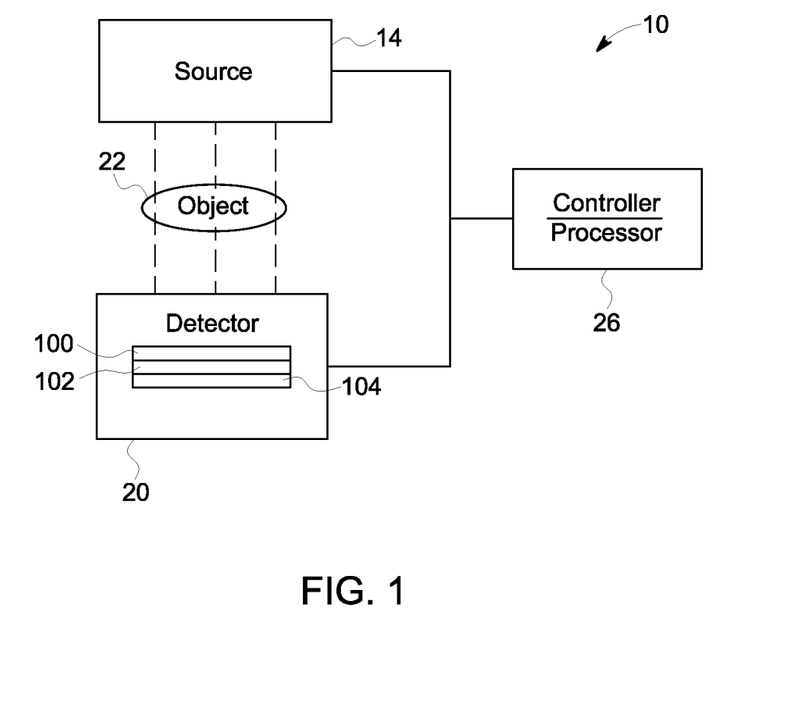
FIG. 1 is a simplified schematic block diagram of an exemplary embodiment of an imaging system.

Referring now to FIG. 1, an imaging system 10 includes a source 14 of electromagnetic energy, one or more detectors 20, and a controller/processor 26. The imaging system 10 also includes an analog-to-digital (A/D) converter assembly 104. The controller/processor 26 may provide power and/or timing signals to the source 14. The detector 20 senses energy emitted by the source 14 that has passed through an object 22 being imaged. In response thereto, the detector 20 produces analog electrical signals that represent the sensed energy. The A/D converter assembly 104 samples the analog data received from the detector 20 and converts the data to digital signals. The controller/processor 26 performs subsequent processing and image reconstruction using the digital signals received from the A/D converter assembly 104. The reconstructed image may be stored and/or displayed by the controller/processor 26 and/or another device.

In the exemplary embodiment, the detector 20 includes a scintillator 100 and photosensor array 102. Accordingly, in the exemplary embodiment, the detector 20 is an indirect conversion detector wherein a scintillator converts electromagnetic energy into visible (or near-UV) light photons. The detector 20 may be any type of indirect conversion detector, such as, but not limited to, an NaI:Tl (thallium-doped sodium iodide) detector. Alternatively, the detector 20 is any type of direct conversion detector, such as, but not limited to, a cadmium zinc telluride (CZT) detector.

The detector 20 includes an analog-to-digital (A/D) converter assembly 104 in the exemplary embodiment. In other words, in the exemplary embodiment, the A/D converter assembly 104 is a component of the detector 20. In some alternative embodiments, the controller/processor 26 includes the A/D converter assembly 104 such that the A/D converter assembly 104 is a component of the controller/processor 26. In still other alternative embodiments, a controller 726 (shown in FIG. 10) includes the A/D converter assembly 104 such that the A/D converter assembly 104 is a component of the controller 726.

Figure 2:
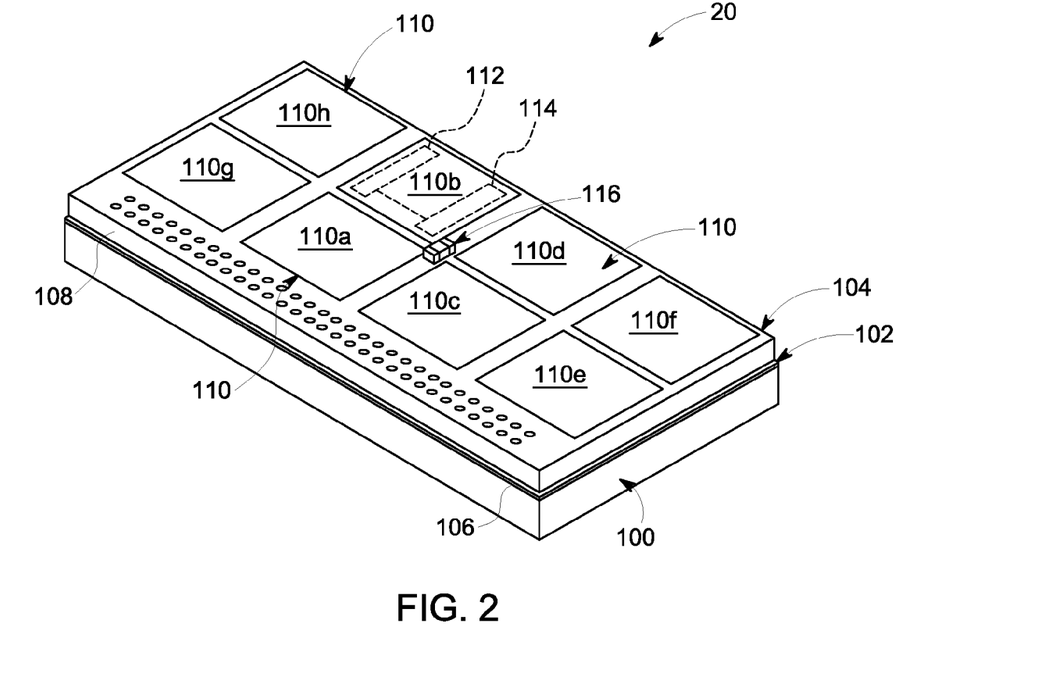
FIG. 2 is a perspective view of a portion of an exemplary embodiment of an imaging detector of the imaging system shown in FIG. 1.

FIG. 2 is a perspective view of a portion of an exemplary embodiment of the detector 20. In the exemplary embodiment, the detector 20 includes the scintillator 100, the photosensor array 102, and the A/D converter assembly 104. The scintillator 100 is fabricated from a scintillating medium that is configured to emit optical photons, or light, in response to the absorption of electromagnetic energy (e.g., x-rays) that has traveled through the object being imaged (e.g., the object 22 shown in FIG. 1 or the patient 722 shown in FIGS. 9 and 10). In response to energy received from a source (e.g., the source 14 shown in FIG. 1 or the x-ray source 714 shown in FIGS. 9 and 10) that has traveled through the object being imaged, the scintillator 100 is configured to emit light that corresponds to pixels in the resulting image.

The photosensor array 102 includes a plurality of individual photosensors (not shown), which may be arranged in a plurality of rows and/or columns on a substrate 106. The substrate 106 may include only a single layer, or may be a multi-layered structure. Each photosensor is a photosensitive element that is configured to absorb light emitted by the scintillator and generate an electrical charge in response thereto. The electrical signals generated by the photosensors are analog signals that correspond to pixels in the resulting image. The photosensors may be any type of photosensor, such as, but not limited to, photodiodes and/or the like.

The A/D converter assembly 104 includes a substrate 108 and one or more A/D converters 110 mounted on the substrate 108. Each A/D converter 110 is operatively connected to one or more corresponding photosensors of the photosensor array 102 for receiving the analog electrical signals generated thereby. For example, the substrate 108 may include circuitry that transmits the analog electrical signals generated by the photosensors to the A/D converters 110. Each A/D converter 110 includes an analog section 112 and a digital section 114. The analog section 112 receives the analog electrical signals generated by the corresponding photosensor(s). The digital section 114 converts the analog electrical signals into digital signals that are used to reconstruct the resulting image.

Although shown as having eight A/D converters 110, the A/D converter assembly 104 may include any number of A/D converters 110. In some embodiments, the number of A/D converters 110 is the same as the number of photosensors of the photosensor array 102 and/or the same as the number of pixels in the resulting image. For example, in some embodiments, each A/D converter 110 is associated with a single corresponding photosensor and/or a single corresponding pixel. Moreover, in some alternative embodiments, the A/D converter assembly 104 includes a plurality of substrates 108 that each holds one or more A/D converters 110. The substrate 108 may include only a single layer or may be comprised of multiple layers.

The A/D converter assembly 104 includes one or more temperature sensors 116 that are configured to measure the temperature of one or more of the A/D converters 110. In the exemplary embodiment, the A/D converter assembly 104 includes a single temperature sensor 116 that is mounted on the substrate 108 proximate four of the A/D converters 110a, 110b, 110c, and 110d. As will be described in more detail below, the measured temperatures of the A/D converters 110a, 110b, 110c, and 110d are used to correct gains of the A/D converters 110 during or after an imaging scan of an object is performed. The temperature sensor 116 may be operatively connected to the controller/processor 26 (FIG. 1) and/or another device of the imaging system 10 for reporting the measured temperatures thereto. Each temperature sensor 116 of the A/D converter assembly 104 may be any type of temperature sensor that is suitable for measuring the temperature of an A/D converter 110.

The A/D converter assembly 104 may include any number of temperature sensors 116 for measuring the temperature of any number of the A/D converters 110 of the assembly 104. As described above, in the exemplary embodiment the A/D converter assembly 104 includes a single temperature sensor 116 that measures the temperature of four out of the eight total A/D converters 110. For the purposes of correcting the gains of the A/D converters 110 as is described below, any of the A/D converters 110 whose temperatures are not measured may be considered to experience the same temperatures as any of the A/D converters 110 whose temperatures are measured during an imaging scan of an object. For example, in the exemplary embodiment, any of the A/D converters 110e, 110f, 110g, and/or 110h may be considered to experience the same temperatures as any of the A/D converters 110a, 110b, 110c, and/or 110e during an imaging scan of an object. Accordingly, the temperatures of all of the A/D converters 110 of the assembly 104 are not necessarily measured to correct the gains of all of the A/D converters 110 as is described below. In some alternative embodiments, the A/D converter assembly 104 includes another temperature sensor 116 that is configured to measure the temperature of the A/D converters 110e and/or 110f, and/or the A/D converter assembly 104 another temperature sensor 112 that is configured to measure the temperature of A/D converters 110g and 110h. In still other alternative embodiments, the A/D converter assembly 104 includes the same number of temperature sensors 116 as the total number of A/D converters 110 of the assembly 104, wherein each temperature sensor 116 is configured to measure the temperature of a corresponding one of the A/D converters 110.

Each temperature sensor 116 of the A/D converter assembly 104 may be mounted at any location within a corresponding A/D converter 110, at any location on the corresponding A/D converter(s) 110, and/or at any location on the substrate 108 proximate the corresponding A/D converter(s) 110 that enables the temperature sensor 116 to measure the temperature of the corresponding A/D converter(s) 110. In some embodiments, a temperature sensor 116 is built into a base material (e.g., a silicon die) of the corresponding A/D converter 110 instead of being a separate and discrete component from the corresponding A/D converter 110. As used herein, an A/D converter 110 "corresponds" to a temperature sensor 116 if the temperature sensor 116 is configured to measure the temperature of the A/D converter 110. In the exemplary embodiment, the temperature sensor 116 is mounted on the substrate 108 proximate the A/D converters 110a-110d for measuring the temperatures thereof. The temperature sensor 116 is optionally engaged with one or more of the A/D converters 110a-110d. In some alternative embodiments, the temperature sensor 116 is mounted on an exterior surface of one or more of the corresponding A/D converters 110a, 110b, 110c, and/or 110d. In other alternative embodiments, the temperature sensor 116 is embedded within one of the A/D converters 110a-d. In embodiments wherein a temperature sensor 116 is embedded within an A/D converter, the temperature sensor 116 is only configured to measure the temperature of the A/D converter within which the temperature sensor 116 is embedded.

Figure 3:
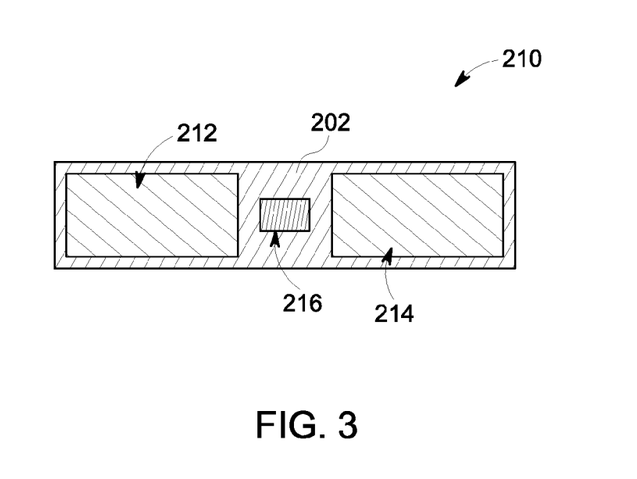
FIG. 3 is a cross-sectional view of an exemplary alternative embodiment of an analog-to-digital (A/D) converter of the imaging detector shown in FIG. 2.

FIG. 3 is a cross-sectional view of an exemplary alternative embodiment of an A/D converter 210, for example for use with the imaging system 10 (shown in FIG. 1), the CT imaging system 710 (shown in FIGS. 9 and 10), and/or the detector 20 (shown in FIGS. 1 and 2). The A/D converter 210 includes an analog section 212, a digital section 214, and a base material 202 that at least partially encapsulates the sections 212 and 214. A temperature sensor 216 is embedded within the A/D converter 210. The temperature sensor 216 is configured to measure the temperature of the A/D converter 210.

In the exemplary embodiment, the temperature sensor 216 is encapsulated within the base material 202 between the analog section 212 and the digital section 214. But, the temperature sensor 216 may be located at any location within the A/D converter 210 that enables the temperature sensor 216 to measure the temperature of the A/D converter. The base material 202 may be any material that enables the A/D converter 210 to convert analog electrical signals into digital signals, such as, but not limited to, silicon and/or the like.

Figure 4:
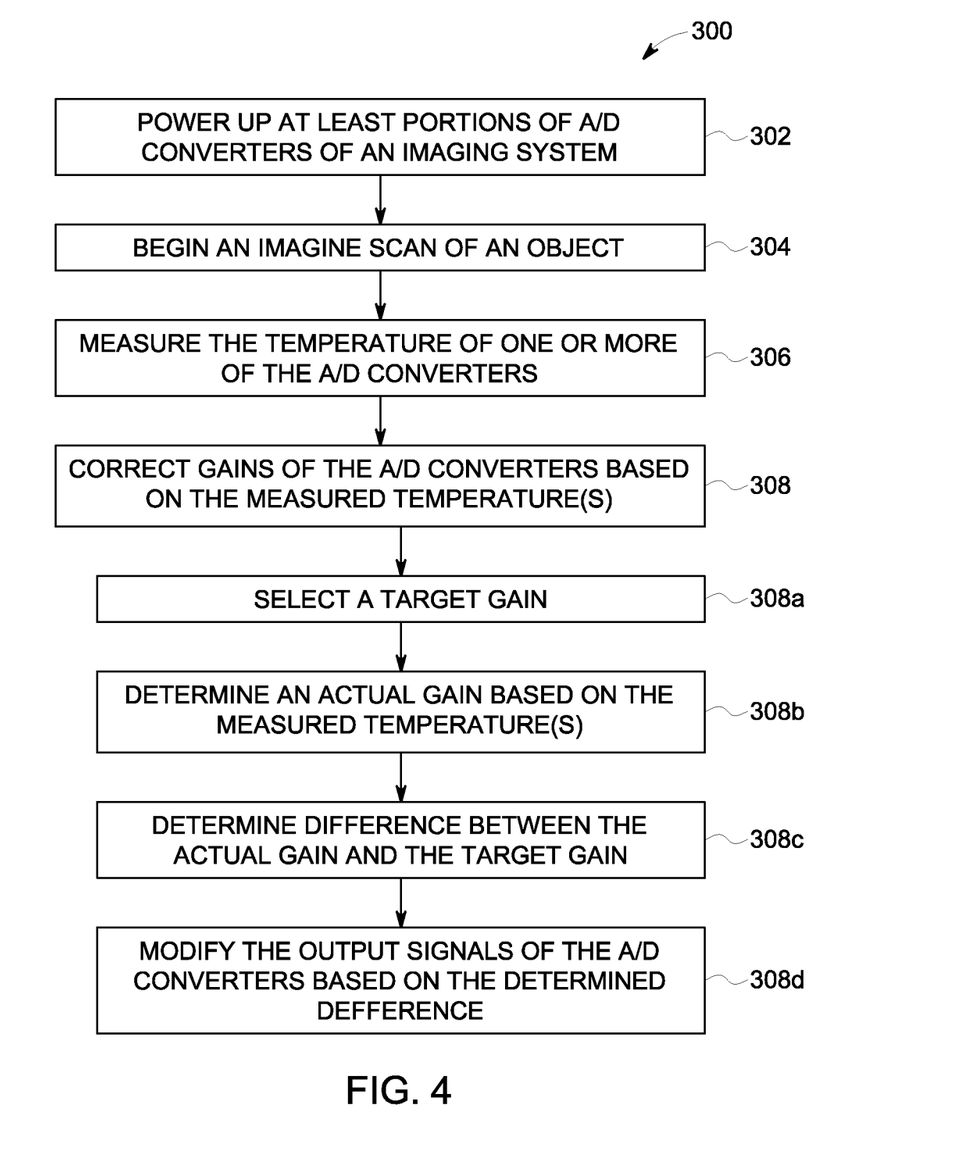
FIG. 4 is a flowchart illustrating an exemplary embodiment of a method for imaging.

FIG. 4 is a flowchart illustrating an exemplary embodiment of a method 300 for imaging, for example using the imaging system 10 (FIG. 1), the CT imaging system 710 (shown in FIGS. 9 and 10), and/or the detector 20 (shown in FIGS. 1 and 2). At 302, the method 300 includes powering up at least portions of A/D converters (e.g., the A/D converters 110 shown in FIG. 2 and/or the A/D converter 210 shown in FIG. 3) of an imaging system at or immediately before a beginning of an imaging scan of an object. The A/D converters are associated with a detector of the imaging system. For example, the A/D converters may be components of the detector or may be components of a controller/processor of the imaging system that are operatively connected to the detector.

As used herein, "powering up" a device means supplying electrical power to the device to enable operation of the device. The portions of the A/D converters that are powered up at 302 were previously powered down, for example after a previous imaging scan, to conserve electrical power when the imaging system was not in use. As used herein, a device is "powered down" when the device is not receiving electrical power and is therefore not operational. In the exemplary embodiment, digital sections (e.g., the digital sections 114 shown in FIG. 2 and/or the digital section 214 shown in FIG. 3) of the A/D converters were powered down and thereafter powered up at 302. In addition or alternatively to the digital sections, in some embodiments analog sections (e.g., the analog sections 112 shown in FIG. 2 and/or the analog section 212 shown in FIG. 3) of the A/D converters were powered down and thereafter powered up at 302. As used herein, "immediately before a beginning of an imaging scan" is defined as any amount of time before the beginning of the imaging scan that is less than the amount of time it takes an A/D converter to reach the normal operating temperature range thereof. The normal operating temperature range may have any size, any temperature values, and/or the like. As used herein, the "beginning" of an imaging scan is the point in time at which the imaging source (e.g., the source 14 shown in FIG. 1 or the source 714 shown in FIGS. 9 and 10) begins to emit electromagnetic energy.

The method 300 optionally includes measuring an initial temperature of one or more of the A/D converters associated with the detector before an imaging scan is begun. At 304, the method 300 includes beginning an imaging scan of an object. When the A/D converters are powered up, the temperature of the A/D converters increases until the A/D converters reach a normal operational temperature range. But, because the A/D converters are powered up at or immediately before the beginning (at 304) of the imaging scan, the A/D converters will not reach the normal operating temperature range until after a portion of the imaging scan has been completed. In other words, the temperatures of the A/D converters increase during at least an initial portion of the imaging scan such that each A/D converter will have different temperatures at different times during the imaging scan. In some embodiments, the A/D converters do not reach the normal operating temperature range thereof during the scan. Because the temperature of the A/D converters affects the gain of the A/D converters, the A/D converters may have different actual gains at different times during the imaging scan. For example, as the temperatures of the A/D converters increase, the actual gains of the A/D converters decrease or increase. Accordingly, the method 300 includes correcting, at 308, the gains of the A/D converters based on the temperature increases of the A/D converters during the imaging scan.

More specifically, at 306, the method 300 includes measuring the temperature of one or more of the A/D converters associated with the detector during the imaging scan. Any A/D converters that are associated with the detector and whose temperatures are not measured may be considered to experience the same temperatures as the A/D converter(s) whose temperature is measured (e.g., adjacent A/D converters). The point in time at which the temperature of the A/D converter(s) is measured corresponds to a detection event of the detector that the A/D converters are associated with. The gains of the A/D converters for the detection event are corrected, at 308, based on the measured temperature(s) of the A/D converter(s). Correcting the gains at 308 includes selecting, at 308*a*, a target gain of the A/D converters. The target gain may be a predetermined gain, which may or may not be equivalent to the value of an actual gain of the A/D converters during the imaging scan. Alternatively, the target gain is selected as the value of an actual gain of the A/D converters during the imaging scan. For example, the target gain may be selected as the value of the actual gain of the A/D converters at the normal operating temperature range of the A/D converters. Moreover, and for example, the target gain may be selected as the value of the actual gain of the A/D converters at the initial temperature that was optionally measured before the imaging scan was begun at 304. As will be described below, the target gain is used to generate a correction factor for correcting the gains.

Figure 5:
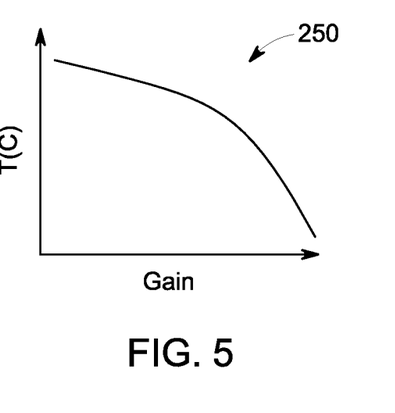
FIG. 5 is a graph illustrating an exemplary embodiment of a predetermined relationship between the temperature and gain of an A/D converter.

At 308*b*, the method 300 includes determining an actual gain of the A/D converters based on the measured temperature(s). The actual gain of the A/D converters is determined at 308*b* using a predetermined relationship between the temperature of the A/D converters and the gain of the A/D converters. The predetermined relationship may be any form of comparison between the temperature and the gain, such as, but not limited to, a graph, a table, and/or the like. For example, FIG. 5 is an exemplary embodiment of a graph 250 of a predetermined relationship between the temperature and gain of an A/D converter. As can be seen in FIG. 5, in the exemplary embodiment, the value of the gain of the A/D converter increases as the temperature of the A/D converter increases. Alternatively, the value of the gain of the A/D converter decreases as the temperature of the A/D converter increases.

Referring again to FIG. 4, at 308*c*, the method 300 includes determining a difference between the actual gain of the A/D converters determined at step 308*b* and the target gain selected at step 308*a*. The difference determined at step 308*c* is the correction factor described above. For example, the difference determined at step 308*c* may be a ratio of the target gain selected at step 308*a* to the actual gain determined at step 308*b*. One example of the correction factor can be represented by the equation: CF=AG/TG, wherein CF is the correction factor, AG is the actual gain determined at step 308*b*, and TG is the target gain selected at step 308*a*. However, the difference determined at step 308*c* may be any other comparison of the actual gain determined at step 308*b* and the target gain selected at step 308*a*. The output signals of the A/D converters are modified, at 308*d*, based on the determined difference between the actual gain and the target gain. The output signals are modified by changing the value of the gain from the value of the actual gain to the value of the target gain. Accordingly, correcting the gains at 308 includes modifying the output signals by changing the value of a gain of an A/D converter based on a difference between a measured temperature of the A/D converter and a temperature of the A/D converter. The output signals 308*d* may be modified at step 308*d* by applying the correction factor to the output signals. For example, modifying the output signals at step 308*d* may include measuring an output signal and then multiplying the actual gain of the output signal by the correction factor.

During the imaging scan, the steps 306 and 308 of the method 300 may be repeated for one or more other detection events of the detector that the A/D converters are associated with. More specifically, the temperature of one or more of the A/D converters associated with the detector is measured, at 306, for one or more other detection events of the detector. The value of the gains of the A/D converters associated with the detector are corrected, at 308, to the value of the target gain for one or more other detection events of the detector. By performing the steps 306 and 308 of the method 300 for all detection events wherein the value of the actual gains of the A/D converters does not match the value of the target gain, each pixel of the resulting image will be generated using the same gain value (or a gain value that is within a predetermined range), which will improve the quality of the resulting image and/or reduce or eliminate errors in the resulting image. In some embodiments, the steps 306 and 308 of the method 300 are performed during the imaging scan for all of the detection events of the detector that the A/D converters are associated with. In embodiments wherein the target gain is selected as the value of the gain of the A/D converters at the normal operating temperature range, the steps 306 and 308 may only be performed for detection events of the detector that occur before the A/D converters reach the normal operating temperature range during the imaging scan.

The gains of the A/D converters may be corrected at 308 during the imaging scan in real time. Alternatively, the gains of the A/D converters are corrected at 308 after the imaging scan has been completed.

Figure 6:
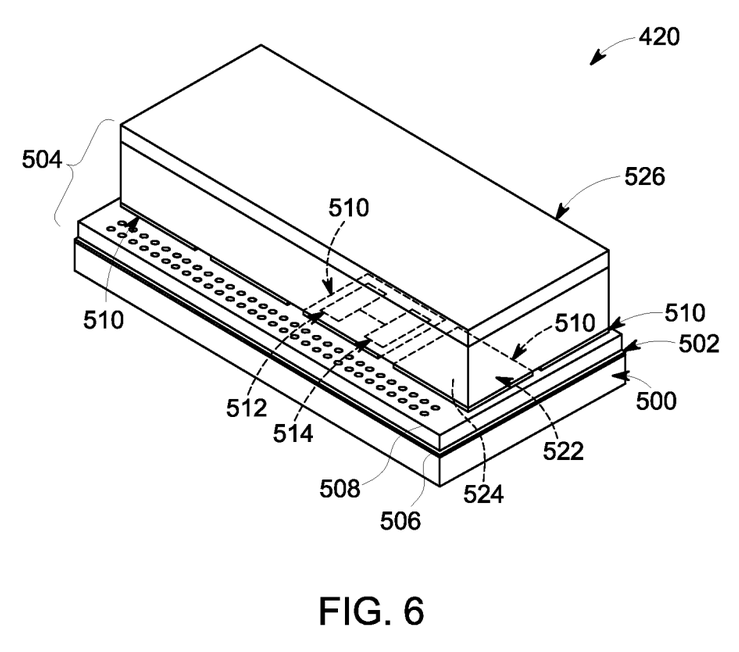
FIG. 6 is a perspective view of a portion of an exemplary alternative embodiment of an imaging detector that may be used with the imaging system shown in FIG. 1.

FIG. 6 is a perspective view of a portion of an exemplary alternative embodiment of an imaging detector 420. The imaging detector 420 may be used with the imaging system 10 (shown in FIG. 1) or the CT imaging system 710 (shown in FIGS. 9 and 10). In the exemplary embodiment, the detector 420 includes a scintillator 500, a photosensor array 502, and an A/D converter assembly 504. The scintillator 500 is fabricated from a scintillating medium that is configured to emit optical photons, or light, in response to the absorption of electromagnetic energy (e.g., x-rays) that has traveled through the object being imaged (e.g., the object 22 shown in FIG. 1 or the patient 722 shown in FIGS. 8 and 9). In response to energy received from a source (e.g., the source 14 shown in FIG. 1 or the x-ray source 714 shown in FIGS. 9 and 10) that has traveled through the object being imaged, the scintillator 500 is configured to emit light that corresponds to pixels in the resulting image.

The photosensor array 502 includes a plurality of individual photosensors (not shown), which may be arranged in a plurality of rows and/or columns on a substrate 506. The substrate 506 may include only a single layer, or may be a multi-layered structure. Each photosensor is a photosensitive element that is configured to absorb light emitted by the scintillator and generate an electrical charge in response thereto. The electrical signals generated by the photosensors are analog signals that correspond to pixels in the resulting image. The photosensors may be any type of photosensor, such as, but not limited to, photodiodes and/or the like.

In the exemplary embodiment, the detector 420 is an indirect conversion detector wherein a scintillator converts electromagnetic energy into visible (or near-UV) light photons. The detector 420 may be any type of indirect conversion detector, such as, but not limited to, an NaI:Tl (thallium-doped sodium iodide) detector. Alternatively, the detector 420 is any type of direct conversion detector, such as, but not limited to, a cadmium zinc telluride (CZT) detector.

The A/D converter assembly 504 includes a substrate 508 and one or more A/D converters 510 mounted on the substrate 508. Each A/D converter 510 is operatively connected to one or more corresponding photosensors of the photosensor array 502 for receiving the analog electrical signals generated thereby. For example, the substrate 508 may include circuitry that transmits the analog electrical signals generated by the photosensors to the A/D converters 510. Each A/D converter 510 includes an analog section 512 and a digital section 514. The analog section 512 receives the analog electrical signals generated by the corresponding photosensor(s). The digital section 514 converts the analog electrical signals into digital signals that are used to reconstruct the resulting image. The A/D converters 510 include outer sides 522 that face away from the substrate 508. The outer sides 522 include surfaces 524.

The A/D converter assembly 504 may include any number of A/D converters 510. In some embodiments, the number of A/D converters 510 is the same as the number of photosensors of the photosensor array 502 and/or the same as the number of pixels in the resulting image. For example, in some embodiments, each A/D converter 510 is associated with a single corresponding photosensor and/or a single corresponding pixel. Moreover, in some alternative embodiments, the A/D converter assembly 504 includes a plurality of substrates 508 that each holds one or more A/D converters 510. The substrate 108 may include only a single layer or may be comprised of multiple layers.

In the exemplary embodiment, the A/D converter assembly 504 is a component of the detector 420. In some alternative embodiments, the controller/processor 26 (FIG. 1) includes the A/D converter assembly 504 such that the A/D converter assembly 504 is a component of the controller/processor 26.

In still other alternative embodiments, the controller 726 (FIG. 10) includes the A/D converter assembly 504 such that the A/D converter assembly 504 is a component of the controller 726.

One or more heat sinks 526 are engaged with the A/D converters 510 for absorbing heat from the A/D converters 510. In the exemplary embodiment, the A/D converter assembly 504 includes a single heat sink 526 that is engaged with each of the A/D converters 510 of the assembly 504. The heat sink 526 absorbs heat from the A/D converters 510 during an imaging scan. As described above, when the A/D converters 510 are powered up, the temperature of the A/D converters 510 increases until the A/D converters 510 reach a normal operational temperature range. If the A/D converters 510 are powered up at or immediately before the beginning of the imaging scan, the A/D converters 510 will not reach the normal operating temperature range until after a portion of the imaging scan has been completed. Because the temperature of the A/D converters 510 affects the gain of the A/D converters 510, the A/D converters 510 may have different actual gains at different times during the imaging scan.

Accordingly, the heat sink 526 is used to absorb heat from the A/D converters 510 during the imaging scan to maintain the temperature change of the A/D converters 510 within a predetermined range during the imaging scan. More specifically, as heat is generated within the A/D converters 510 during the imaging scan, the heat sink 526 absorbs the heat such that the A/D converters 510 do not experience an increase in temperature that is outside the predetermined range during the imaging scan. The predetermined range may represent a sensitivity limit of the A/D converters 510 to temperature change. In other words, the predetermined range may by the range of temperature change wherein the gains of the A/D converters 510 do not change enough to cause errors and/or artifacts within the resulting image. Each pixel of the resulting image will therefore be generated using the same gain value or a gain value that is within a range that does not cause errors and/or artifacts within the resulting image. The heat sink 526 may or may not dissipate the heat absorbed from the A/D converters 510 to a fluid medium (e.g., ambient air). The predetermined range may have any size, include any values, and/or the like, such as, but not limited to, a size of half of a degree Celsius, a size of a whole degree Celsius, a size of two degrees Celsius, and/or the like The heat sink 526 may be engaged in general thermal contact with any surface(s) of the A/D converters 510 that enables the heat sink 526 to absorb heat from the A/D converters 510. In the exemplary embodiment, the heat sink 526 is engaged with the surfaces 524 of the outer sides 522 of the A/D converters 510.

The heat sink 526 may be fabricated from any material(s) that enable the heat sink 526 to absorb heat from the A/D converters 510. The material(s), geometry, and/or the like of the heat sink 526 may be selected to absorb a predetermined amount of heat from the A/D converters 510, to absorb heat from the A/D converters 510 at a predetermined rate, and/or the like. For example, the heat sink 526 has a heat capacity that is capable of limiting the temperature change of the A/D converters to within the predetermined range during the imaging scan. In some embodiments, the heat sink 526 only has enough heat capacity to limit the temperature change of the A/D converters to within the predetermined range for the duration of the imaging scan. Accordingly, the heat capacity of the heat sink 526 may be selected based on an expected duration of the imaging scan. Optionally, the heat sink 526 includes a phase change material that is configured to absorb and release heat when the material changes phases. For example, the phase change material may absorb heat when the material changes from a solid to a liquid and release heat when the material changes from a liquid to a solid. Examples of suitable phase change material includes, but are not limited to, paraffin wax and/or the like. When the heat sink 526 includes a phase change material, the heat sink 526 may be configured to maintain the A/D converters 510 at a substantially constant temperature during the imaging scan.

In the exemplary embodiment, a single heat sink 526 is engaged with all of the A/D converters 510 of the A/D converter assembly 504. In some alternative embodiments, the A/D converter assembly 504 includes a plurality of heat sinks 526 that are each engaged with one or more A/D converters 510. The A/D converter assembly 504 may include any number of heat sinks 526 for absorbing heat from any number of A/D converters 510. Although shown as having the general shape of a parallelepiped, the heat sink 526 may additionally or alternatively include any other shape(s).

Figure 7:
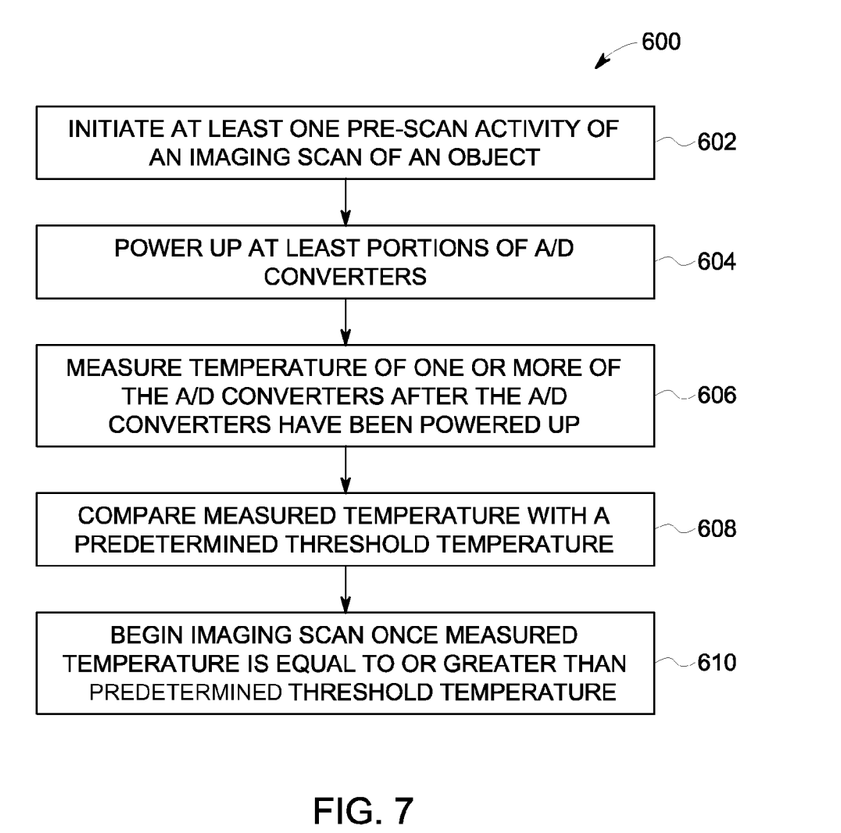
FIG. 7 is a flowchart illustrating an exemplary alternative embodiment of a method for imaging.

FIG. 7 is a flowchart illustrating an exemplary alternative embodiment of a method 600 for imaging, for example using the imaging system 10 (shown in FIG. 1), the CT imaging system 710 (shown in FIGS. 9 and 10), and/or the detector 20 (shown in FIGS. 1 and 2). Because there is typically a time lag between when pre-scan activities of an imaging scan are initiated and when the imaging scan begins, there is a time window to bring the A/D converters of an imaging system up to temperature. At 602, the method 600 includes initiating at least one pre-scan activity of an imaging scan of an object. The pre-scan activities may include any activity that is necessary to perform before the imaging scan begins, such as, but not limited to, entering patient information into the imaging system, entering a type of imaging scan to be performed into the imaging system, entering an identification of an object (e.g., a person, a container, etc.) or a portion (e.g., an organ, a body part, etc.) of an object to be scanned into the imaging system, entering a milliamp value of a source (e.g., the source 14 shown in FIG. 1 or the source 714 shown in FIGS. 9 and 10) of electromagnetic energy, entering a kilovolt value of the source of electromagnetic energy, entering a number of slices, and/or the like.

At 604, the method 600 includes powering up at least portions of A/D converters (e.g., the A/D converters 110 shown in FIG. 2 and/or the A/D converter 210 shown in FIG. 3) of the imaging system upon initiation, at 602, of the at least one pre-scan activity. The A/D converters are associated with a detector of the imaging system. For example, the A/D converters may be components of the detector or may be components of a controller/processor of the imaging system that are operatively connected to the detector. The portions of the A/D converters that are powered up at 604 were previously powered down, for example after a previous imaging scan, to conserve electrical power when the imaging system was not in use. In other words, the method 600 may be considered to include powering down at least portions of the A/D converters before initiation, at 602, of the at least one pre-scan activity. In the exemplary embodiment, digital sections (e.g., the digital sections 114 shown in FIG. 2 and/or the digital section 214 shown in FIG. 3) of the A/D converters were powered down and thereafter powered up at 604. In addition or alternatively to the digital sections, in some embodiments analog sections (e.g., the analog sections 112 shown in FIG. 2 and/or the analog section 212 shown in FIG. 3) of the A/D converters were powered down and thereafter powered up at 604.

When the A/D converters are powered up, the temperature of the A/D converters increases until the A/D converters reach a normal operational temperature range. At 606, the method 600 includes measuring the temperature of one or more of the A/D converters associated with the detector after the A/D converters have been powered up at 604. Any A/D converters that are associated with the detector and whose temperatures are not measured may be considered to experience the same temperatures as the A/D converter(s) whose temperature is measured. The measured temperature of the A/D converter(s) is compared with a predetermined threshold temperature at 608. Optionally, the predetermined threshold temperature is within the normal operating temperature range of the A/D converters. The predetermined threshold temperature represents a sensitivity limit of the A/D converters 510 to temperature change. In other words, the predetermined threshold temperature is the lower limit of a sensitivity range of temperature change wherein the gains of the A/D converters 510 do not change enough to cause errors and/or artifacts within the resulting image. The sensitivity range includes the normal operating temperature range therein, however, the predetermined threshold temperature is optionally lower than the lower limit of the normal operating temperature range. In some embodiments, the predetermined threshold temperature is the lower limit of the normal operating temperature range. The method 600 includes beginning, at 610, the imaging scan once the measured temperature of the A/D converter(s) is equal to or greater than the predetermined threshold temperature. Optionally, the method 600 includes powering down at least a portion of the A/D converters after the imaging scan has been completed.

By waiting to begin the imaging scan until the A/D converters have reached a temperature equal to or greater than the predetermined threshold temperature, each pixel of the resulting image may be generated using the same gain value or a gain value that is within a range that does not cause errors and/or artifacts within the resulting image.

Figure 8:
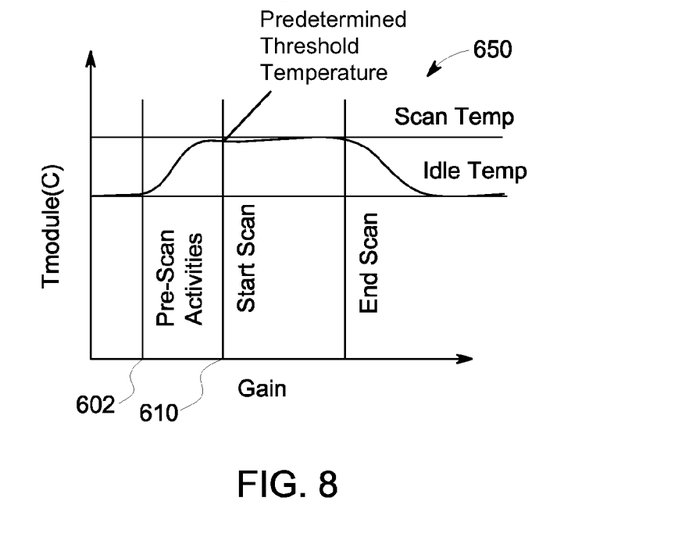
FIG. 8 is a graph illustrating an exemplary embodiment of a predetermined relationship between the temperature and gain of an A/D converter.

FIG. 8 illustrates an exemplary embodiment of a graph 650 of a predetermined relationship between the temperature and gain of an A/D converter. As can be seen in FIG. 8, the temperatures of the A/D converters rise during the pre-scan activities initiated at step 602 of the method 600. Once the A/D converters reach the predetermined threshold temperature, the imaging scan is begun at 610. In an exemplary embodiment, the predetermined threshold temperature is lower than the lower limit of the normal operating temperature range. As can be seen in FIG. 8, after the imaging scan is begun at 610, the temperatures of the A/D converters increase during the scan from the predetermined threshold temperature to within the normal operating temperature range. The A/D converters remain within the normal operating temperature range during the remainder of the imaging scan. Once the imaging scan is completed, at least portions of the A/D converters are powered down to conserve electrical power.

Figure 9:
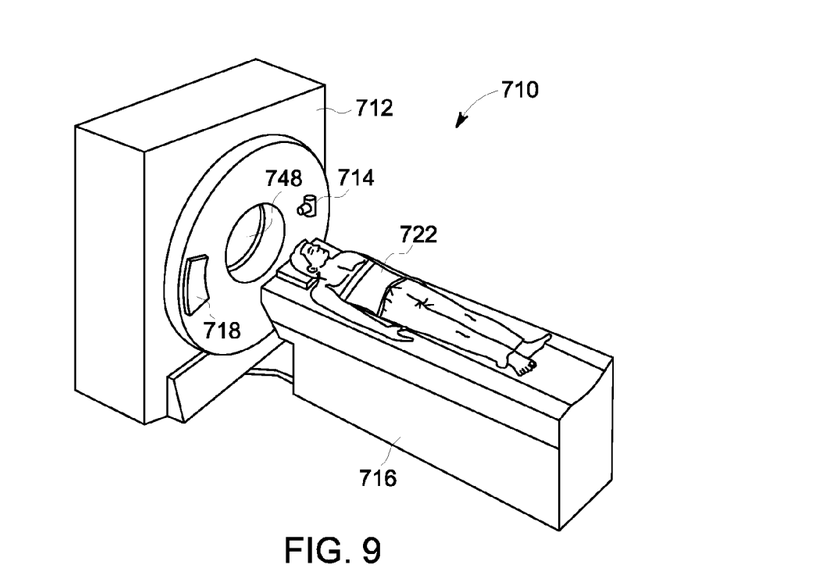
FIG. 9 is a pictorial drawing of an exemplary embodiment of a computed tomography (CT) imaging system.
Figure 10:
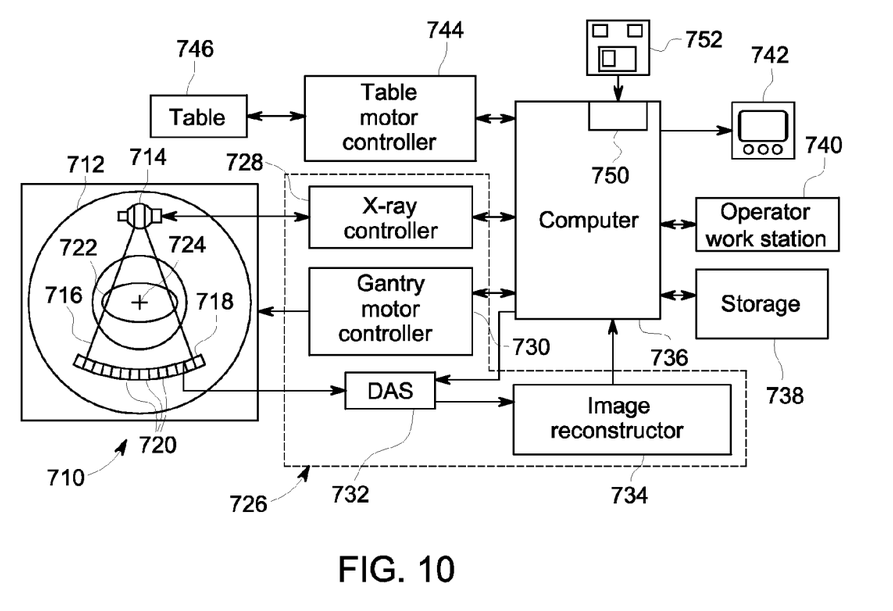
FIG. 10 is a schematic block diagram of the CT imaging system shown in FIG. 9.

Referring to FIGS. 9 and 10, a multi-slice scanning imaging system, for example, a CT imaging system 710 is shown as including a plurality of detectors 720. The CT imaging system 710 includes a gantry 712, which includes an x-ray tube 714 (also referred to as an x-ray source 714 herein) that projects a beam of x-rays 716 toward a detector array 718 on the opposite side of the gantry 712. The detector array 718 is formed by a plurality of detector rows (not shown) including a plurality of the detectors 720 that together sense the projected x-rays that pass through an object, such as a medical patient 722 between the array 718 and the source 714. Each detector 720 produces an electrical signal that represents the intensity of an impinging x-ray beam and hence can be used to estimate the attenuation of the beam as the beam passes through the patient 722. During a scan to acquire x-ray projection data, the gantry 712 and the components mounted therein rotate about a center of rotation 724. FIG. 10 shows only a single row of detectors 720 (i.e., a detector row). However, the multi-slice detector array 718 includes a plurality of parallel detector rows of detectors 720 such that projection data corresponding to a plurality of quasi-parallel or parallel slices can be acquired simultaneously during a scan.

Rotation of components on the gantry 712 and the operation of the x-ray source 714 are controlled by a controller 726 of the CT imaging system 710. The controller 726 includes an x-ray controller 728 that provides power and timing signals to the x-ray source 714 and a gantry motor controller 730 that controls the rotational speed and position of components on the gantry 712. The CT imaging system 710 may include a data acquisition system (DAS) 732 in the controller 726 that samples analog data from the detectors 720 and converts the data to digital signals for subsequent processing. Alternatively, the DAS 732 or a portion thereof (e.g., A/D converters) is a component of the detectors 720. An image reconstructor 734 of the controller 726 receives sampled and digitized x-ray data from the DAS 732 and performs high-speed image reconstruction. The reconstructed image is applied as an input to a computer 736 that stores the image in a storage device 738. The image reconstructor 734 can be specialized hardware or computer programs executing in the controller 726 or on the computer 736. The controller 726, the computer 736, and/or the image reconstructor 734 may be implemented as components of the controller/processor 26 shown in FIG. 1, for example.

The computer 736 also receives commands and scanning parameters from an operator via a console 740 that has a keyboard and/or other user input and/or marking devices, such as a mouse, trackball, or light pen. An associated display 742, examples of which include a cathode ray tube (CRT) display, liquid crystal display (LCD), or plasma display, allows the operator to observe the reconstructed image and other data from the computer 736. The display 742 may include a user pointing device, such as a pressure-sensitive input screen. The operator supplied commands and parameters are used by the computer 736 to provide control signals and information to the DAS 732, x-ray controller 728, and gantry motor controller 730. In addition, the computer 736 operates a table motor controller 744 that controls a motorized table 746 to position the patient 722 in the gantry 712. For example, the table 746 moves portions of the patient 722 through a gantry opening 748.

In one embodiment, the computer 736 includes a device 750, for example, a floppy disk drive, CD-ROM drive, DVD drive, magnetic optical disk (MOD) device, or any other device including a network connecting device such as an Ethernet device for reading instructions and/or data from a computer-readable medium 752, such as a floppy disk, a CD-ROM, a DVD or another source such as a network or the Internet, as well as yet to be developed digital means. In another embodiment, the computer 736 executes instructions stored in firmware (not shown).

As used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein. Further, the CT imaging system may be, for example, different types of CT imaging systems, such as a third generation CT imaging system, a fourth generation CT imaging system (stationary detector—rotating x-ray source) and a fifth generation CT imaging system (stationary detector and x-ray source), as well as first and second generation CT imaging systems. Additionally, as described above, it is contemplated that the benefits of the various embodiments accrue to imaging modalities other than CT and energies other than x-rays. Further, as also described above, although the herein described methods and apparatus are described in a medical setting, it is contemplated that the benefits of the various embodiments accrue to non-human imaging systems such as, but not limited to, those systems typically employed in an animal imaging, in security applications, and/or in industrial inspection applications.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for image detection comprising:
  measuring a temperature of an analog-to-digital (A/D) converter of an imaging system during an imaging scan of an object;
  powering up at least a portion of the A/D converter at or immediately before a beginning of the imaging scan; and
  correcting a gain of the A/D converter based on the measured temperature of the A/D converter, wherein correcting a gain of the A/D converter based on the measured temperature of the A/D converter comprises correcting a gain of the A/D converter based on an increase in the temperature of the A/D converter during the imaging scan.

2. The method of claim 1, wherein correcting a gain of the A/D converter based on the measured temperature of the A/D converter comprises using a predetermined relationship between the temperature of the A/D converter and the gain of the A/D converter.

3. The method of claim 1, wherein correcting a gain of the A/D converter based on the measured temperature of the A/D converter comprises correcting the gain during the imaging scan of the object.

4. The method of claim 1, wherein correcting a gain of the A/D converter based on the measured temperature of the A/D converter comprises correcting the gain after the imaging scan of the object has been completed.

5. The method of claim 1, wherein the imaging system comprises a computed tomography (CT) imaging system.

6. An imaging system comprising:
  a detector configured to generate analog electrical signals in response to received electromagnetic energy;
  an analog-to-digital (A/D) converter mounted on a substrate and operatively connected to the detector for receiving the analog electrical signals generated by the detector, the A/D converter being configured to convert the analog electrical signals into digital electrical signals, the A/D converter comprising an outer side that faces away from the substrate; and
  a heat sink engaged with the outer side of the A/D converter for absorbing heat from the A/D converter, wherein the heat sink is configured to absorb heat from the A/D converter during an imaging scan to maintain a temperature change of the A/D converter during the scan within a predetermined range.

7. The system of claim 6, wherein the A/D converter and the heat sink are components of the detector of the imaging system.

8. The system of claim 6, further comprising a controller that is operatively connected to the detector, the controller comprising the A/D converter and the heat sink.

9. An imaging system comprising:
  a detector configured to generate analog electrical signals in response to received electromagnetic energy;
  an analog-to-digital (A/D) converter operatively connected to the detector for receiving the analog electrical signals generated by the detector, the A/D converter being configured to convert the analog electrical signals into digital electrical signals; and
  a heat sink engaged with a surface of the A/D converter for absorbing heat from the A/D converter, wherein the heat sink is configured to absorb heat from the A/D converter during an imaging scan to maintain a temperature change of the A/D converter during the scan within a predetermined range;
  wherein the A/D converter comprises a plurality of A/D converters mounted on a common substrate, the heat sink being engaged with at least two of the plurality of A/D converters.

10. A method for image detection comprising:
  initiating at least one pre-scan activity of an imaging scan of an object;
  powering up at least a portion of an analog-to-digital (A/D) converter upon initiation of the at least one pre-scan activity;
  measuring a temperature of the A/D converter after the A/D converter has been powered up; and
  beginning the imaging scan once the measured temperature of the A/D converter is equal to or greater than a predetermined threshold temperature.

11. The method of claim 10, wherein the at least one pre-scan activity comprises at least one of entering patient information, entering a type of imaging scan to be performed, or entering an identification of an object or a portion of an object to be scanned, entering a milliamp value of a source of electromagnetic energy, entering a kilovolt value of the source of electromagnetic energy, or entering a number of slices.

12. The method of claim 10, wherein the predetermined threshold temperature at least one of within a normal operating temperature range of the A/D converter or a sensitivity limit of the A/D converters to temperature change.

13. The method of claim 10, wherein powering up at least a portion of an A/D converter upon initiation of the at least one pre-scan activity comprises powering up a digital section of the A/D converter.

* * * * *